United States Patent [19]

Valentine

[11] Patent Number: 4,787,845

[45] Date of Patent: Nov. 29, 1988

[54] ORAL IRRIGATOR

[76] Inventor: Rodney F. Valentine, 121 Glenview Dr., Des Moines, Iowa 50312

[21] Appl. No.: 26,035

[22] Filed: Mar. 16, 1987

[51] Int. Cl.⁴ .............................................. A61G 17/02
[52] U.S. Cl. ........................................ 433/88; 433/80; 604/39; 128/66; 239/543; 51/439
[58] Field of Search .................... 604/39, 30, 100, 145, 604/119; 433/84, 87, 88, 91, 92, 95, 99, 102, 80; 239/95, 154, 543, 602; 51/439

[56]  References Cited

U.S. PATENT DOCUMENTS

| | | | |
|---|---|---|---|
| 1,494,809 | 5/1924 | Sahr | 433/91 X |
| 2,757,688 | 8/1956 | Saladin | |
| 3,675,645 | 7/1972 | Samarin | |
| 3,807,048 | 4/1974 | Malmin | |
| 4,173,828 | 11/1979 | Lustig et al. | 433/87 |
| 4,174,571 | 11/1979 | Gallant | 433/88 X |
| 4,276,880 | 7/1981 | Malmin | |
| 4,676,749 | 6/1987 | Mabille | 433/88 |

Primary Examiner—Larry Jones
Attorney, Agent, or Firm—Rudolph L. Lowell

[57]  ABSTRACT

A device for use in oral and dental hygiene wherein an oral irrigator is provided for connection to a conventional syringe or the like for applying fluid under pressure to the irrigator. The irrigator has a downwardly tapered tip with one or more longitudinally formed channels fluidly connected to the fluid supply syringe, with the remaining circumference of the irrigator tip capable of holding away the gum tissue, whereby irrigating fluid under pressure is applied into the base of a periodontal pocket for cleansing purposes with the channels also providing an exit for the fluid and debris to prevent undue pressure build-up.

5 Claims, 1 Drawing Sheet

U.S. Patent  Nov. 29, 1988  4,787,845
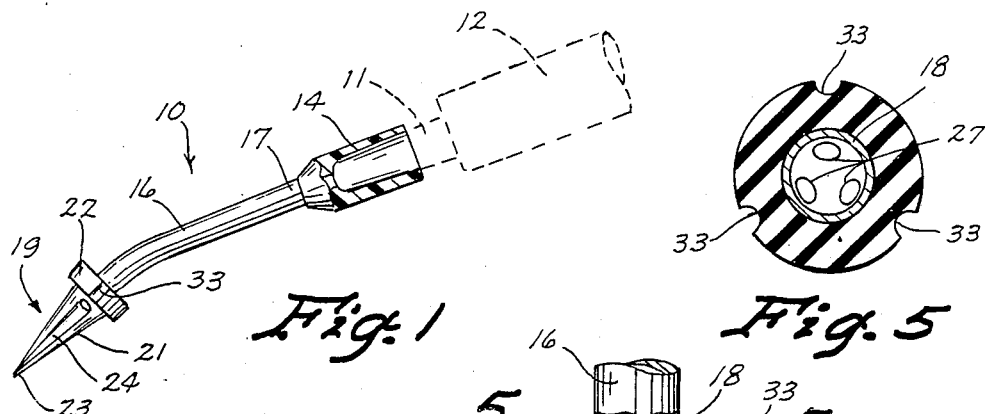
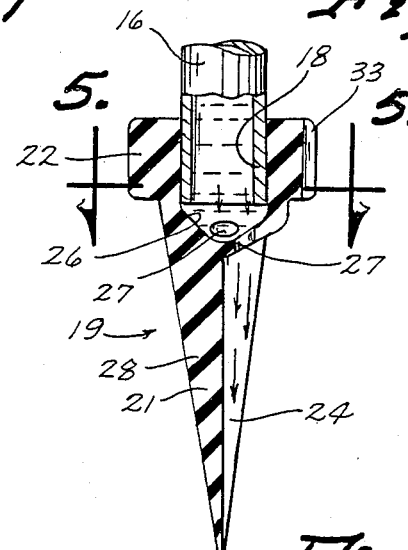
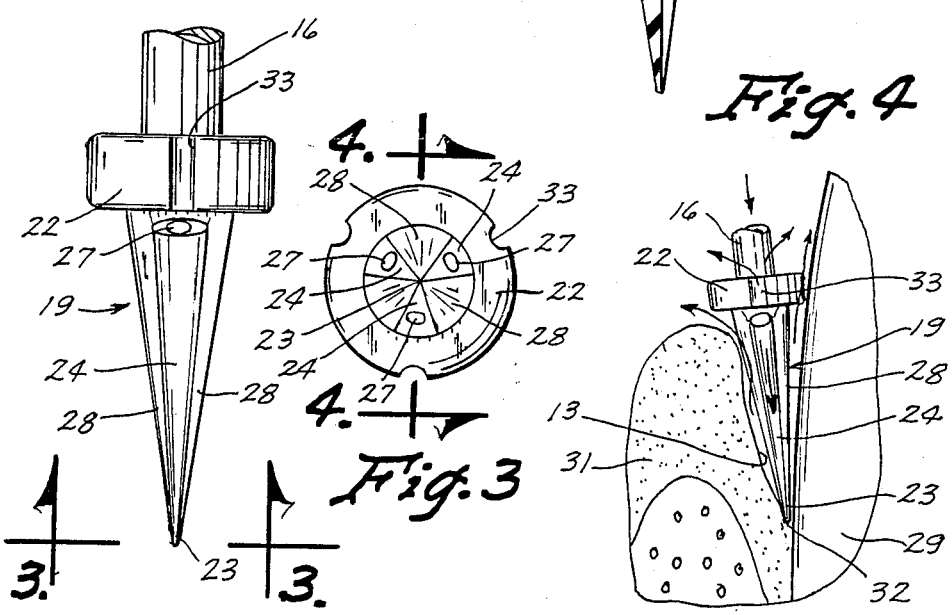
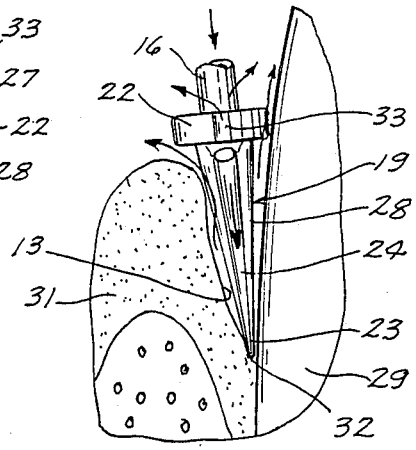

ORAL IRRIGATOR

TECHNICAL FIELD

The present invention relates to dental and oral hygiene devices for irrigating and cleansing periodontal pockets, and more particularly to an oral irrigator usable by both physicians and patients.

BACKGROUND ART

Dental and oral hygenic devices for periodontal pocket cleaning are known, but heretofore have been relatively ineffective and limited in scope.

It is known, for example, that using common teeth cleaning devices such as toothbrushes, dental floss, and water pressure activated devices do not reach into the entire pocket in order to properly cleanse them of food debris and bacteria found there.

Another device shown inferentially in U.S. Pat. No. 4,276,880 to Malmin discloses a hollow rigid member termed a "cannula", needle-like in shape and dimensions, used to root canal work; however one embodiment shows it bent at right angles and with a window opening formed near a closed end for irrigation and aspiration purposes to a periodontal pocket.

Another needle-type irrigator is shown in Malmin U.S. Pat. No. 3,807,048. Samiran et al. U.S. Pat. No. 3,675,645 shows a rotatable tooth engaging, tapered element having ribs and fluid passages for teeth cleaning purposes.

DISCLOSURE OF THE INVENTION

To overcome the inadequacies of the prior art, the present invention is provided. The present oral irrigator is adapted to be fluid connected to any irrigating or irrigating-aspirating type syringe for supplying cleansing fluid thereto.

The irrigator itself comprises a hub for syringe connection, a slightly curved hollow stem leading from the hub, a circular collar having circumferentially spaced safety grooves formed therein for pressure relief, and a downwardly tapered tip fluidly open to the stem. Within and about the circumference of the tip, a plurality of longitudinally extended vanes or channels are formed, each channel extended substantially the entire length of the tip such that the cleansing fluid flows substantially parallel the longitudinal axis of the tip and to its outermost end. Formation of the longitudinal channels within the circumferential area of the tip leaves circumferentially spaced segments which act to hold the gum tissue away from the channels, thus permitting relative free flow of the fluid to and from the entire pocket.

It is an object of this invention to provide a new and novel oral irrigator.

It is another object of this invention to provide an improved oral irrigator capable of effective use by both professional and non-professional and to promote confidence for the non-professional in its use.

A further object of this invention is to provide an oral irrigator capable of delivering fluid to the greatest depth of a periodontal pocket for full and effective irrigation without causing excessive fluid pressure therein.

Still another object of this invention is the provision of an oral irrigator which enables the operator to use the tip thereof as a feeler to locate the periodontal pocket and also to insert the tip between the teeth.

Yet another object of this invention is to provide an oral irrigator tip capable of delivering fluid to the base of the periodontal pocket while preventing the gum tissue from acting to seal off the fluid opening.

It is yet another object of this invention to provide an oral irrigator tip having a collar member which acts as a safety valve in that it is provided with circumferential grooves such that should the operator force the tip too far into the soft gum tissue whereby the collar is substantially surrounded by tissue and root, the grooves allow the fluid forced into the pocket to exit therefrom without building up pressure.

BRIEF DESCRIPTION OF THE DRAWINGS

These and other objects of the invention will become readily apparent upon a thorough study and review of the following detailed description of the preferred embodiment for carrying out the invention, particularly when viewed in conjunction with the accompanying drawings, wherein:

FIG. 1 is perspective view of the oral irrigator of this invention shown by the use of dotted lines attached to a section of a syringe;

FIG. 2 is an enlarged plan view of the oral irrigator tip, and showing partially a stem element thereof;

FIG. 3 is an end elevational view as taken along the line 3—3 in FIG. 2;

FIG. 4 is a cross-sectional view as taken along the line 4—4 in FIG. 3;

FIG. 5 is a cross-sectional view as taken along the line 5—5 in FIG. 4; and

FIG. 6 is a reduced sectional diagrammatic view showing application of the oral irrigator to the cleaning of a periodontal pocket.

BEST MODE FOR CARRYING OUT THE INVENTION

Referring now to the drawings, the oral irrigator of this invention is indicated generally at (10) in FIG. 1, and is shown removably attached to the discharge end (11) of a conventional syringe (12) for delivering cleansing fluid under pressure to a periodontal pocket (13)(FIG. 6).

The oral irrigator (10) comprises an open-ended, hollow hub (14) adapted to receive the syringe discharge end (11); an elongated, hollow stem (16) secured at one end (17)—or integral therewith as the case may be, with the hub (14), and having a free end (18) (FIG. 4) open for the passage of fluid therethrough. A tip element (19) is secured to the free end (18) to receive fluid therefrom, and the tip (19) has a conical body (21) tapered from a large, hub end (22) to a pointed, smaller end (23).

As best shown in FIGS. 2-5, a plurality of channels (24) are formed circumferentially about and within said conical body (21), and are extended longitudinally thereof substantially the entire length of the tip (19)(See FIG. 4). In this manner, fluid from the syringe (12) can pass through the hub (14) and stem (16) to the tip (19) from whence it is discharged parallel of the longitudinal axis of the conical body (21).

More particularly, the large hub end (22) of the tip has an inner cavity (26) formed therein to receive the stem free end (18) and fluid, and is further provided with a passage (27)(FIG. 4) formed therein at the upper end of each channel (24), which passage is disposed parallel the longitudinal axis of the conical body (21) in order to direct fluid longitudinally parallel to the longitudinal axis of the conical body (21).

The channels (24) themselves are cut into the circumference of the body (21) in a V-like shape (See FIG. 3) in cross-section, and form thereby a plurality of segments (28) therebetween the segments (28) also extendend longitudinally the length of the conical body (21). Referring to FIG. 4, it is seen that each channel (24) is open its entire length of the conical body (21) from its passage (27) to the periphery of the conical body (21) whereby cleansing fluid is dispensed, as shown by the arrows outwardly of each channel (24), the entire length thereof, and particularly to the smaller, pointed end (23) of the tip (19).

It is recommended that the oral irrigator tip (19) be made of a material that is resilient and rubber-like, is smooth and easily cleaned. The length of the conical body (21) should be such that it will extend into a periodontal pocket (13) up to approximately nine mm. deep. In operation, the oral irrigator (10) is hand operated, and with the resilient tip (19) can be guided even by the non-professional—the patient, such that the conical body (21) is inserted into the pocket (13) between a root (29) and adjacent gum tissue (31), with the smaller pointed end (23) at the base (32) of the pocket (13).

With the oral irrigator (10) fitted onto, for example, a plastic syringe such as a Luer-Lok the irrigator (10) can be used by either the physician at the office, or the patient at home, to deliver both irrigating and/or medicating fluids. The irrigator (10) thus delivers fluid to the greatest depth of the periodontal pocket (13) without causing excess pressure.

The segments act to hold the tissue (31) away from the channels (24) in such a way that the soft tissue (31) does not act as a seal, and help in maintaining a V-like shape for the channels (24) thereby aiding in the transmission of fluid downwardly of the tip (19) toward its outer, pointed end (23) and into the base (32) (FIG. 6). To provide a safety valve—in effect, grooves (33) (FIG. 5) are formed within and are disposed about the periphery of the hub (22), the grooves (33) extended substantially parallel the channels (24). Thus, should fluid exit through the channels (24) be blocked by the hub (22) being pressed too far into the pocket (13), or by being completely surrounded by tissue (31) and root (29), such as to form a seal, fluid can escape through the grooves (33).

The oral irrigator can be used on both buccal and lingual, and between the teeth to deliver fluid. The structure of the irrigator (10) permits its use to massage the gingiva and the tooth while the fluid from the channels (24) is flowing. The low pressure massaging action will dislodge plaque and the fluid will then carry away the plaque and its toxic products.

I claim:

1. An oral irrigator for attachment to and use with an instrument capable of selectively supplying fluid under pressure to the oral irrigator comprising:
    means for fluid attachment to the instrument;
    stem means fluidly secured to said attachment means and having an open free end; and
    tip means having a conical body fluidly secured to said stem means free end, said body tapered from a large end adjacent to said free end to a pointed end, one or more channels formed circumferentially about and within said body and extended longitudinally thereof, whereby fluid can be emitted at said pointed end, said large end having one or more grooves formed therein and disposed about its periphery, said grooves extended substantially parallel said channels.

2. An oral irrigator for attachment to and use with an instrument capable of selectively supplying fluid under pressure to the oral irrigator comprising:
    means for fluid attachment to the instrument;
    stem means fluidly secured to said attachment means and having an open free end; and
    tip means having a conical body with a large end tapering to a small end, said large end attached to said free end, and a plurality of channels formed within said conical body and extended longitudinally thereof, said channels each having one end thereof fluidly connected to said free end and each channel open to the periphery of said conical body substantially the entire length thereof, said large end having one or more grooves formed therein and disposed about its periphery, said grooves extended substantially parallel said channels.

3. An oral irrigator tip comprising:
    a conical body having a large end and a small end and tapered from said large end to the small end;
    said large end having a fluid receiving cavity formed therein for connection to a fluid transmitting element; and
    one or more channels formed in and about the circumference of said conical body, each channel extended longitudinally of and substantially the entire length of said conical body, and having one end open to said cavity for receiving fluid therefrom for flow to the small end of said conical body.

4. An oral irrigator tip as described in claim 3 and further wherein each said claimed is open its entire length to the periphery of said conical body.

5. An oral irrigator tip as described in claim 3, wherein a fluid passage is formed in said conical body between said cavity and the one end of each channel, each said fluid passage extended parallel to the longitudinal axis of said conical body, whereby fluid is transmitted through each fluid passage and into an associated channel for flow parallel to the said axis of said conical body toward said small end thereof.

* * * * *